US00PP25530P2

(12) United States Plant Patent
Kordes

(10) Patent No.: US PP25,530 P2
(45) Date of Patent: May 12, 2015

(54) HYBRID TEA ROSE PLANT NAMED 'KORGOTFUN'

(50) Latin Name: *Rosa hybrida*
Varietal Denomination: KORgotfun

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 92 days.

(21) Appl. No.: 13/987,687

(22) Filed: Aug. 20, 2013

(51) Int. Cl.
*A01H 5/00* (2006.01)

(52) U.S. Cl.
USPC ..... Plt./132

(58) Field of Classification Search
CPC ..... A01H 5/0222; A01H 5/0216
USPC ..... Plt./132, 130
See application file for complete search history.

*Primary Examiner* — Kent L Bell

(57) ABSTRACT

A new and distinct variety of rose with long lasting, novel bi-color yellow-pink flowers, and attractive foliage with very good disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORgotfun'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2003. The crossing was between an 'un-named seedling', the seed parent, and another 'un-named seedling', the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORgotfun'.

SUMMARY OF THE INVENTION

The new rose plant may be distinguished from its seed parent, an 'un-named seedling', by the following combination of characteristics:

1. 'KORgotfun' has a nostalgic flower shape, whereas the 'un-named seedling' has a pointed flower shape.
2. 'KORgotfun' has a high resistance to blackspot, whereas the 'un-named seedling' has an average resistance.

The new rose plant may be distinguished from its pollen parent, an 'un-named seedling', by the following combination of characteristics:

1. 'KORgotfun' has a bi-color yellow and pink flower, whereas the 'un-named seedling' has a yellow flower.
2. 'KORgotfun' has a very double petal count, whereas the 'un-named seedling' has a semi-double petal count.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORgotfun' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORgotfun' was selected in May 2004 from the seedling beds to be asexually propagated for further evaluation. The first asexual propagation of 'KORgotfun' was done by budding in July 2004 at the inventor's nursery in Offenseth-Sparrieshoop, Germany.

These initial and other subsequent propagations conducted in controlled environments demonstrate that 'KORgotfun' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORgotfun'.

DETAILED BOTANICAL DESCRIPTION

The following is a description of 'KORgotfun', as observed growing in June 2013 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORaruli', a rose variety from the same inventor described and illustrated in U.S. Plant Pat. No. 22,352 and issued on Dec. 20, 2011 are compared to 'KORgotfun' in Chart 1.

CHART 1

| Characteristic | 'KORgotfun' | 'KORaruli' |
|---|---|---|
| Bud form | Short, globular | Long, high centered |
| Petal count | 100-110 | 45 |
| Prickle incidence (average per 10 cm of stem) | 15 | 60-80 |

Parents:

*Seed parent*.—An 'un-named seedling'.

*Pollen parent*.—An 'un-named seedling'.

Classification:

*Botanical classification*.—*Rosa hybrida* 'KORgotfun'.

*Commercial classification*.—Hybrid Tea rose.

FLOWER AND FLOWER BUD

Blooming habit: Continuous. Floriferous.

Flower bud:

*Size*.—Upon opening, 40 mm in length from base of receptacle to distal end of bud and 20 mm diameter at its widest point.

*Bud form*.—Short. Globular.

*Bud color*.—As sepals first unfold, bud color is Red Group 53B to Red Group 46B. When ¼ open, the upper surface of petals is White Group 155B in middle zone with basal zone Yellow Group 11A and intonations of Red-Purple Group 61C in marginal zone. The lower surface is Yellow-Orange Group 16B in the basal zone, Red Group 47C in the middle zone, and Red Group 48A in the marginal zone.

*Sepals*.—Color: Upper surface Yellow-Green Group 146C. Lower surface Yellow-Green Group 146C. Size: Average 20-22 mm (l)×10-13 mm (w). Shape: Weak foliaceous appendages on 3 of the five sepals. Apex: Apiculate. Base: Flat at union with receptacle. Quantity: Five. Surface texture: Upper side: Very pubescent. Lower surface: Moderately pubescent. Margins: Lightly pubescent. Stipitate glands: Few to none.

Flower bloom:

*Fragrance*.—Light.

*Duration*.—On the plant 5-8 days. As a cut flower, 4-5 days. Senesced petals drop away cleanly.

*Size*.—Large for a hybrid tea rose. When open, the average flower diameter is 130 mm and the average flower height is 60 mm.

*Form*.—Shape of flower when viewed from the side: Upon opening, upper part: Flat. Upon opening, lower part: Flat. Open flower, upper part: Flattened convex. Open flower, lower part: Flat.

Color:

*Upon opening, petals*.—

*Outermost petals*.—Outer Side: Yellow-Orange Group 15A with intonations of Red Group 43C on marginal zone. Inner Side: Yellow-Orange Group 14B with intonations of Red Group 46D in marginal zone.

*Innermost petals*.—Outer Side: Yellow-Orange Group 14D. Inner Side: Yellow Group 13C in basal zone to Yellow-Orange Group 15D.

Upon opening, basal petal spots: No distinctive coloration at petal base observed. After opening, petals:

*Outermost petals*.—Outer Side: Yellow Group 13D in basal zone, Yellow Group 13D with intonations of Red Group 43D in middle zone, and Red-Purple Group 61C in marginal zone. Inner Side: Yellow Group 13D in basal zone, Yellow Group 13D with intonations of Red Group 43D in middle zone, and Red-Purple Group 61C in marginal zone.

*Innermost petals*.—Outer Side: Yellow Group 8A in basal zone, Yellow Group 8D in middle zone, and Red Group 53D in marginal zone. Inner Side: Yellow Group 8A in basal zone, Yellow Group 8D in middle zone, and Red Group 38B in marginal zone.

After opening, basal petal spots: No distinctive coloration at petal base observed.

General tonality: On open flower bi-color Yellow-Orange Group 16D with Red Group 47D. No change in the general tonality at the end of the $4^{th}$ day. Afterwards, general tonality is Yellow Group 8D with Red Group 53C.

Petals:

*Petal count*.—Very Double.

*Average range*.—Approximately 100-110 petals under normal conditions.

*Petal reflex*.—Petals reflex somewhat.

*Petal margin*.—Retuse.

*Petal shape*.—Obovate. Apex: Retuse. Base: Cuneate.

*Petal size*.—Outer petals: 60 mm (l)×50 mm (w). Inner petals: 35 mm (l)×20 mm (w).

*Thickness*.—Thick.

*Petal arrangement*.—Not formal.

*Texture*.—Satiny.

Petaloids:

*Petaloid count*.—Average of 15-20 per flower.

*Petaloid size*.—3-15 mm (l)×3-8 mm (w).

*Petaloid color*.—Inner side: Yellow-Orange Group 14B. Outer side: Yellow Group 9B.

*Petaloid texture*.—Smooth.

*Margins*.—Undulated.

*Petaloid shape*.—Most commonly obovate. Apex: Obtuse. Base: Attenuate.

Reproductive organs:

*Pistils*.—Average. Approximately 55-60 present. Stigmas: Location: Slightly inferior in position to anthers. Color: Yellow-Orange Group 17D. Styles: Length: About 9 mm long. Color: Yellow-Green Group 145D. Intonations of Red Group 47B.

*Stamens*.—Approximately 65-70 on average and regularly arranged. Anthers: Size: Average 3 mm (l)×1 mm (w). Color: Greyed-Orange Group 163B. Pollen: Generally present. Color: Greyed-Orange Group 163C. Filaments: Color: Greyed-Orange Group N163D. Length: 10 mm.

*Receptacle*.—Color: Yellow-Green Group 146C. Intonations of Greyed-Purple Group 183D. Shape: Urn-shaped. Texture: Smooth. Size: 10 mm (h)×18 mm (w).

*Peduncle*.—Length: 70-90 mm average length. Diameter: 4-5 mm average diameter. Color: Yellow-Green Group 146C. Intonations of Greyed-Purple Group 183B. Heavy anthocyanin, typically over 80% of peduncle. Strength: Very strong. Texture: Leathery. Borne: Singularly. Flowers held upright.

THE PLANT

*Growth*.—Vigorous.

*Plant habit*.—Upright to bushy. When grown as a budded field plant, the average plant height is 130 cm and the average plant width is 7 cm.

*Stems*.—Stem color: Young wood: Yellow-Green Group 146B. Older wood: Yellow-Green Group 146A. Stem surface texture: Young wood: Smooth. Older wood: Rough.

*Prickles*.—Present. Incidence: Average of 15 per each 10 cm of stem. Size: Average length: 7 mm. Color: Immature prickles: Greyed-Purple Group 183B. Mature prickles: Greyed-Purple Group 187B. Senescing to Greyed-Brown Group 199A Shape: Deeply concave.

*Leaves*.—Normally 5 leaflets on normal leaves in middle of the stem. Venation pattern: Pyramidal net pattern. Leaf size: 160 mm (l)×120 mm (w). Abundance: Average.

*Leaflets*.—Size: Average size of the terminal leaflet is 65-80 mm (l)×55-60 mm (w). Shape: Ovate. Base: Obtuse. Apex: Acute. Margins: Serrated. Surface: Upper side of leaflet: Semi-glossy. Lower side of leaflet: Matte. Texture: Upper side of leaflet: Leathery. Under side of leaflet: Smooth. Color, mature foliage: Upper Leaflet Surface: Yellow-Green Group 147A. Lower Leaflet Surface: Yellow-Green Group 147B. Color, juvenile foliage: Upper Leaflet Surface: Yellow-Green Group 147A. Lower Leaflet Surface: Yellow-Green Group 147B. Anthocyanin intonation: Greyed-Purple Group 183C. Location: Entire new leaf. Arrangement: Odd pinnate. Venation: Reticulate.

*Stipules*.—Size: 30-34 mm (l)×7-9 mm (w). Stipule color: Yellow-Green Group 146B. Anthocyanin: Greyed-Red Group 182C. Stipitate glands: Limited. Margins: With stipitate glands. Texture: Smooth. Shape: Apex: Apiculate. Base: Winged.

*Petiole*.—Length: Average 30 mm. Diameter: Average 4 mm. Petiole color: Yellow-Green Group 146B. Underneath: Yellow-Green Group 146C. Margins: With very limited numbers of stipitate glands. Prickles: Present. Stipitate Glands: Limited. Texture: Leathery.

*Petiole rachis*.—Length: Average 30 mm. Diameter: Average 3 mm. Color: Yellow-Green Group 146C. Prickles: A few small prickles underneath. Stipitate glands: Limited.

Hips/seed formation: None observed.

Winter hardiness: To date, the variety has been grown successfully in Zone 6.

Disease resistance: Average resistance to Powdery mildew (*Sphaerotheca pannosa*) and very good resistance to blackspot (*Diplocarpon rosae*) diseases under normal growing conditions in Jackson County, Oreg.

I claim:

1. A new and distinct variety of rose plant, as described and illustrated herein.

* * * * *

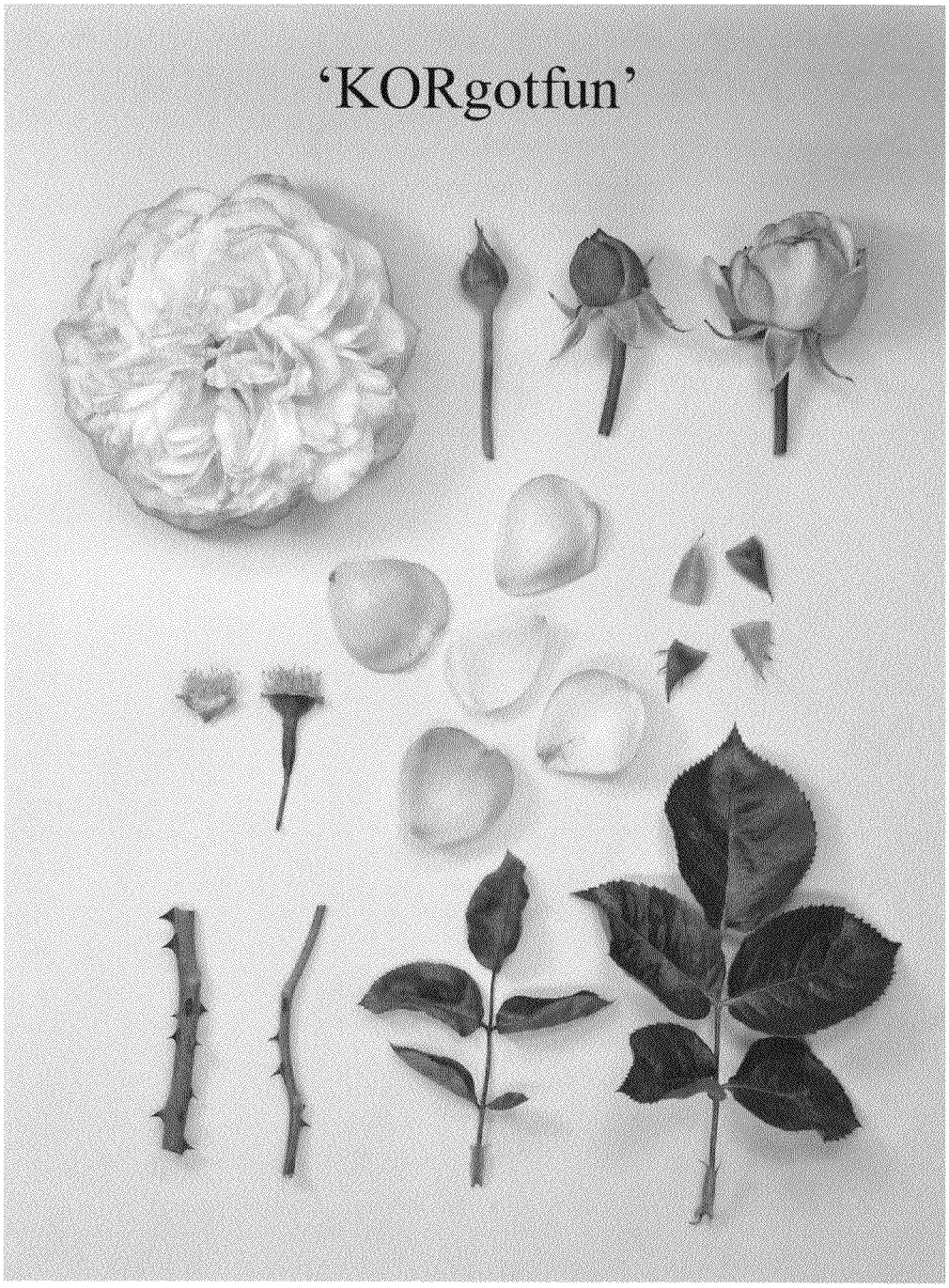
'KORgotfun'